(12) United States Patent
Wang

(10) Patent No.: US 8,998,978 B2
(45) Date of Patent: Apr. 7, 2015

(54) STENT FORMED FROM BIOERODIBLE METAL-BIOCERAMIC COMPOSITE

(75) Inventor: Yunbing Wang, Sunnyvale, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 455 days.

(21) Appl. No.: 11/864,737

(22) Filed: Sep. 28, 2007

(65) Prior Publication Data
US 2009/0088834 A1    Apr. 2, 2009

(51) Int. Cl.
*A61F 2/06*    (2013.01)
*A61L 31/14*   (2006.01)
*A61L 31/12*   (2006.01)

(52) U.S. Cl.
CPC ............. *A61L 31/148* (2013.01); *A61L 31/124* (2013.01)

(58) Field of Classification Search
USPC ......................................................... 623/1.38
See application file for complete search history.

(56) References Cited

U.S. PATENT DOCUMENTS

| | | | |
|---|---|---|---|
| 5,711,763 A * | 1/1998 | Nonami et al. ................ 424/423 |
| 6,013,106 A * | 1/2000 | Tweden et al. ............. 623/11.11 |
| 6,099,561 A * | 8/2000 | Alt ................................ 623/1.44 |
| 6,270,831 B2 * | 8/2001 | Kumar et al. ................ 427/2.24 |
| 8,057,534 B2 * | 11/2011 | Boismier et al. ............ 623/1.38 |
| 8,267,992 B2 * | 9/2012 | Atanasoska et al. ........ 623/1.42 |
| 2003/0219466 A1 * | 11/2003 | Kumta et al. ................ 424/423 |
| 2005/0163954 A1 * | 7/2005 | Shaw ........................... 428/36.1 |
| 2005/0278015 A1 * | 12/2005 | Dave et al. .................. 623/1.38 |
| 2005/0283229 A1 | 12/2005 | Dugan et al. |
| 2006/0052863 A1 | 3/2006 | Harder et al. |
| 2006/0229711 A1 * | 10/2006 | Yan et al. ..................... 623/1.38 |
| 2007/0135905 A1 * | 6/2007 | Burgermeister et al. .... 623/1.38 |
| 2007/0224244 A1 | 9/2007 | Weber et al. |
| 2007/0278720 A1 | 12/2007 | Wang et al. |
| 2007/0282426 A1 | 12/2007 | Wang et al. |
| 2007/0282431 A1 | 12/2007 | Gale et al. |
| 2007/0282434 A1 | 12/2007 | Wang et al. |
| 2007/0288084 A1 * | 12/2007 | Lee et al. ..................... 623/1.16 |
| 2008/0058919 A1 | 3/2008 | Kramer-Brown et al. |
| 2008/0081063 A1 | 4/2008 | Wang et al. |
| 2010/0222873 A1 * | 9/2010 | Atanasoska et al. ........ 623/1.42 |
| 2012/0053674 A1 * | 3/2012 | Boismier et al. ............ 623/1.15 |
| 2012/0070650 A1 * | 3/2012 | Han et al. ..................... 428/327 |

FOREIGN PATENT DOCUMENTS

| | | |
|---|---|---|
| EP | 1 600 178 | 11/2005 |
| JP | 2003-325654 | 11/2003 |
| WO | WO 2006/108065 | 10/2006 |

OTHER PUBLICATIONS

U.S. Appl. No. 11/706,550, filed Feb. 14, 2007, Huang et al.
U.S. Appl. No. 11/823,931, filed Jun. 29, 2007, Wang et al.
U.S. Appl. No. 11/796,226, filed Apr. 26, 2007, Wu.
International Search Report for PCT/US2008/077246, mailed Jan. 15, 2010, 7 pgs.
Witte et al., "Biodegradable magnesium-hydroxyapatite metal matrix composites", Biomaterials 28, pp. 2163-2174 (2007).
Translation of Notice of Reasons for Rejection issued by JPO for appl. No. 2010-527066, 3 pgs. dispatched Nov. 13, 2012.

* cited by examiner

*Primary Examiner* — Jacqueline Woznicki
(74) *Attorney, Agent, or Firm* — Squire Patton Boggs (US) LLP

(57) ABSTRACT

Medical devices and methods of fabricating such medical devices, such as stents, formed at least in part from a metal matrix composite including bioceramic particles dispersed within an erodible metal are disclosed.

6 Claims, 1 Drawing Sheet

STENT FORMED FROM BIOERODIBLE METAL-BIOCERAMIC COMPOSITE

BACKGROUND OF THE INVENTION

1. Field of the Invention

This invention relates to implantable medical devices, in particular stents, fabricated from bioerodable metal matrix composites.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Coronary stents made from non-erodible metals have become the standard of care for percutaneous coronary intervention (PCI) since such stents have been shown to be capable of preventing early and later recoil and restenosis. Despite the positive success of such stents in PCI, a drawback of such durably implanted stents is that the permanent interaction between the stent and surrounding tissue can pose a risk of endothelial dysfunction and late thrombosis.

Thus, it may be desirable for a stent to be biodegradable or bioerodible. In many treatment applications, the presence of a stent in a body may be necessary for a limited period of time until its intended function of, for example, maintaining vascular patency and/or drug delivery is accomplished. Therefore, stents fabricated from bioerodable materials such as bioerodable metals can be configured to completely erode only after the clinical need for them has ended.

SUMMARY OF THE INVENTION

Various embodiments of the present invention include a stent comprising a stent body formed from a metal matrix composite, the composite including erodible bioceramic particles dispersed within an erodible metal, wherein the dispersed bioceramic particles modify the erosion rate of the stent body in a vascular environment and enhance the mechanical properties of the stent body.

Further embodiments of the present invention include a stent comprising a stent body formed from a metal matrix composite, the composite including hydroxyapatite particles dispersed within magnesium, wherein the dispersed bioceramic particles decrease the erosion rate of the stent body in a vascular environment and enhance the mechanical properties of the stent body.

Additional embodiments of the present invention include a method of making a stent comprising: processing bioceramic particles with an erodible metal to form a composite including the bioceramic particles dispersed in the metal, wherein the metal and the particles are processed with a shear stress higher than the fracture strength of clusters of agglomerated bioceramic particles so that agglomeration of the particles is reduced; forming a tube from the composite; and fabricating a stent from the tube, wherein the dispersed bioceramic particles modify the erosion rate of the stent body in a vascular environment and enhance the mechanical properties of the stent body.

DETAILED DESCRIPTION OF THE INVENTION

Various embodiments of the present invention relate to implantable medical devices fabricated from a metal matrix composite including an erodible metal matrix with bioceramic particles dispersed within the matrix. As used herein, an "implantable medical device" includes, but is not limited to, self-expandable stents, balloon-expandable stents, stent-grafts, and generally tubular medical devices.

In certain embodiments, an implantable medical device can be designed for the localized delivery of a therapeutic agent. A medicated implantable medical device may be constructed by coating the device or substrate with a coating material containing a therapeutic agent. The substrate of the device may also contain a therapeutic agent.

Figure 1:
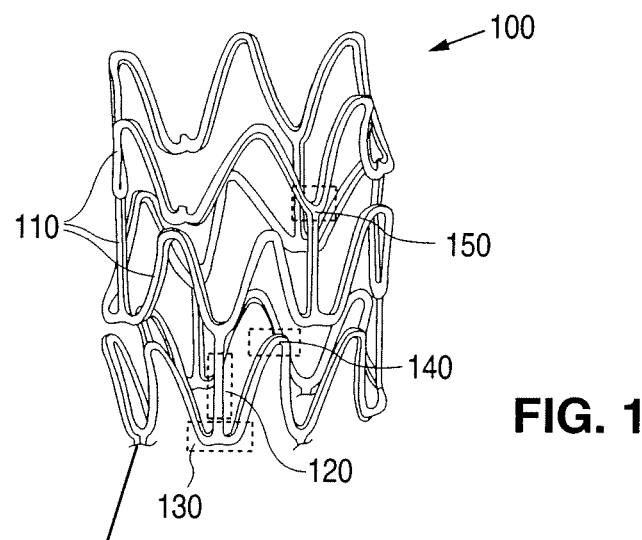
FIG. 1 depicts a view of a stent.

FIG. 1 depicts a view of a stent 100. In some embodiments, a stent may include a pattern or network of interconnecting structural elements 110. Stent 100 may be formed from a tube (not shown). Stent 100 includes a pattern of structural elements 110, which can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern in the tube with a technique such as laser cutting or chemical etching.

The geometry or shape of an implantable medical device may vary throughout its structure to allow radial expansion and compression. A pattern may include portions of structural elements or struts that are straight or relatively straight, an example being a portion 120. In addition, patterns may include structural elements or struts that include curved or bent portions such as portions 130, 140, and 150.

While stents have typically been constructed of relatively inert metals in order to ensure their longevity, degradable or erodible stent structures have more recently been devised in an effort to provide support for only a limited period of time. In general, the support or patency provided by a stent for the treatment of a stenosis is required only for a limited period of time. For example, a preferred or required treatment time by a stent may be less than 18 months, less than a year, between three and 12 months, or more narrowly, between four and eight months.

Throughout a desired treatment period an erodible or degradable stent should be capable of supporting the inward radial force imposed by the lumen walls, including the cyclic loading induced by the beating heart. The stent should maintain such patency in spite of the degradation or erosion of the stent body. Thus, the stent should have sufficient strength, stiffness (modulus), and creep resistance to reduce or eliminate recoil during the treatment period. Furthermore, the stent should be sufficiently tough to resist failure or fracture of the structural elements of a stent. One measure of toughness is the area under a stress-strain or load elongation curve from zero strain to the strain at fracture. Therefore, the modulus, stress at failure (strength), and elongation at failure are relevant to the toughness of a polymer. The bending regions of a typical stent structure are the most susceptible to failure during use. Therefore, an erodible stent structure should have the appropriate combination of mechanical properties and degradation or erosion properties to allow patency during a specified treatment period.

The terms degrade, absorb, erode, as well as degraded, absorbed, eroded, are used interchangeably and refer to materials that are capable of being completely eroded, or absorbed when exposed to bodily conditions. Such materials may be capable of being gradually resorbed, absorbed, and/or eliminated by the body.

"Corrosion" generally refers to the deterioration of essential properties in a metal due to reactions with its surroundings. Corrosion of a metal can occur upon contact with a variety of materials including air, water, organic solvents, etc. As it is used herein, corrosion refers to deterioration or degradation of a metal due to contact with water, such as bodily fluids containing water in a vascular environment. The degradation can result in deterioration mechanical properties of a metallic construct and mass loss from the construct.

Corrosion in an environment that contains moisture involves a series of reactions that result in removal of metal atoms from the metal surface. Corrosion resulting from contact with bodily fluids containing water results in oxidation of the metal (loss of electron(s)) as the metal reacts with water and oxygen. The metal atoms at the surface lose electrons and become actively charged ions that leave the metal to form salts in solution. Corrosion reactions generally involve oxidation and reduction reactions. The metal is oxidized with subsequent reduction of hydrogen ions and oxygen in solution. The reduction reactions drive the oxidation reactions.

"Passivation" is the spontaneous formation of a hard non-reactive surface film that reduces, inhibits, or eliminates further corrosion. Corrosion reactions can result in the formation of this non-reactive layer or film on the surface of the corroding metal. The film is typically a metal oxide, hydroxide, or nitride. For example, corrosion of iron results in formation of iron oxides or hydroxide, while corrosion of magnesium results in magnesium hydroxide formation. The conditions necessary for passivation are recorded in Pourbaix diagrams of metals.

The degree and time frame of passivity or corrosion-resistance depends upon the solubility of materials that form the surface layer. There is a high degree of passivity if the solubility of the layer is low or insoluble. There is no passivity if the materials that would form the protective layer are soluble. As a result, the materials go directly into solution as they are formed, rather than form the protective layer.

Various environmental factors can influence the rate of corrosion including, but not limited, to hydrogen-ion concentration (pH) in the solution, influence of oxygen in solution adjacent to the metal, specific nature and concentration of other ions in solution, rate of flow of the solution in contact with the metal, ability of environment to form a protective deposit or layer on the metal, temperature, and cyclic stress (corrosion fatigue). In particular, a change in pH can influence corrosion by affecting reaction kinetics of the corrosion reactions and by affecting the passivation or ability to form a protective layer. With regard to passivation, the ability to form a protective layer can depend on the solubility of protective layer materials. The solubility of these materials can depend on the pH of the corrosive environment.

Many erodible metals and metal alloys, such as magnesium, iron, zinc, tungsten, and there alloys, may be promising as stent materials. However, these and other metals may not provide a desired combination of degradation and mechanical behavior for a stent during a desired treatment period. In particular, certain metals, such as magnesium, may degrade too quickly, exhibiting a degradation time that is shorter than a desired treatment time. Additionally, such metals may not provide a desired degree of patency or support for a desired time period. An exemplary desired degree of patency is no less than 50% of the deployed diameter of the stent. Alternatively, other metals, such as iron, may degrade too slowly. "Degradation time" refers to the time for a stent implanted in a vessel to completely absorb in vivo. "Degradation time" can also refer to the time for a stent to completely absorb in vitro. Reducing degradation time allows further surgery or intervention, if necessary, on a treated vessel to occur sooner. Additionally decreasing degradation time helps reduces the risk of late thrombosis.

For example, a study on the use of magnesium biodegradable stents in heart patients found that four months after implantation most had degraded. Science News, Jun. 9, 2007, Vol. 171 Issue 23, p 356-357. Heublein et al. conducted a series of in vitro and in vivo preclinical trials using stents made of magnesium alloy. Heublein B, Rohde R, Kaese V, et al. Heart 2003; 89:651-656. These studies demonstrated relatively high rates of degradation from 60 to 90 days, while the overall integrity of the stent remained at 28 days. Ibid. A series of animal studies in which magnesium alloy stents were implanted in porcine coronary arteries demonstrated complete absorption of the stent at 56 days. Ibid.

Peuster et al. reported on experimental studies with absorbable iron stents implanted into the descending aorta of New Zealand white rabbits. Peuster M, Wohlsein P, Brugmann M, et al. Heart 2001; 86:563-569. Angiography at 6, 12, and 18 months after the implantation showed complete patency of the descending aorta in all rabbits with a vessel patency rate of 100%. Ibid.

Previously reported techniques of modifying erosion and mechanical properties include varying the composition of metal alloy components. Eg., U.S. Pat. No. 6,287,332. Simply reducing the dimensions of a metallic implantable medical device in order to reduce residence times may not be a viable option due the compromise in strength that necessarily results. Increasing dimensions to increase degradation time can lead to an undesirably large stent profile.

Thus, approaches are needed for adjusting or tailoring in vivo erosion rates and mechanical properties of erodible metallic stents. In particular, it is desirable to adjust the erosion rate of the stent without unacceptably compromising mechanical properties such as strength.

Various embodiments of the present invention include a stent having a stent body formed at least in part from a metal matrix composite, the composite including bioceramic particles dispersed within an erodible metal. The bioceramic particles can also be erodible. A "composite" refers generally to a material in which two or more distinct, structurally complementary substances combine to produce structural or functional properties not present in any individual components. In some embodiments, the dispersed bioceramic particles modify the in vivo erosion rate of metallic matrix, and thus, of the composite and the stent body. Additionally or alternatively, the bioceramic particles can enhance the mechanical properties of the composite, and thus, the stent body. It has been shown that the corrosive and mechanical properties of a bioceramic magnesium metal alloy composite are adjustable due to the bioceramic particles. Biomaterials 28 (2007) 2163-2174.

In the various embodiments described, a portion, all, or substantially all of the stent body can be formed from the composite. In some embodiments, one or more structural elements or struts of a stent can be fabricated from the composite. In other such embodiments, the body, scaffolding, or substrate of a stent can be made from the composite. The stent body, scaffolding, or substrate may be primarily responsible for providing mechanical support to walls of a bodily lumen once the stent is deployed within the bodily lumen. A stent body, scaffolding, or substrate can refer to a stent structure with an outer surface to which no coating or layer of material different from that of which the structure is manufactured. If the body is manufactured by a coating process, the stent body can refer to a state prior to application of additional coating layers of different material. By "outer surface" is meant any surface however spatially oriented that is in contact with bodily tissue or fluids. A stent body, scaffolding, or substrate can refer to a stent structure formed by laser cutting a pattern into a tube or a sheet that has been rolled into a cylindrical shape.

Figure 2A:
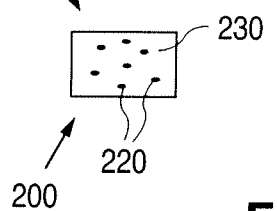
FIG. 2A depicts a section of a structural element from a stent.
Figure 2B:
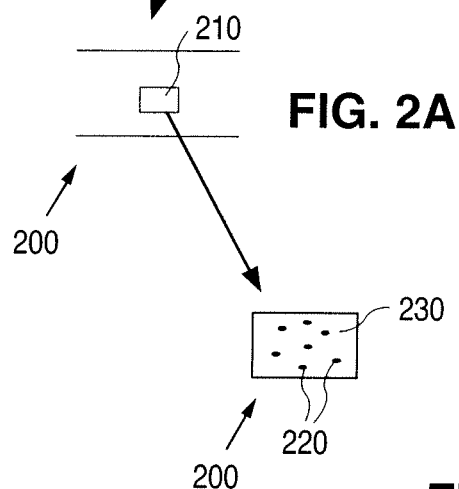
FIG. 2B depicts an expanded view of a portion of a stent section.

FIG. 2A depicts a section 200 of a structural element 110 from stent 100. A portion 210 of section 200 is shown in an expanded view in FIG. 2B. FIG. 2B depicts bioceramic particles 220 dispersed throughout an erodible metallic matrix 230.

Various sizes of the bioceramic particles may be used in the composite. For example, the bioceramic particles can include, but are not limited to, nanoparticles and/or micro particles. A nanoparticle refers to a particle with a characteristic length (e.g., diameter) in the range of about 1-1,000 nm, or more narrowly in the range of 1-100 nm. A microparticle refers to a particle with a characteristic length in the range of greater than 1,000 nm and less than about 10 micrometers. Additionally, bioceramic particles can be of various shapes, including but not limited to, spheres and fibers.

In certain embodiments, the erosion rate of the metallic matrix can be modified by adjusting the pH local to the stent. Local regions refer to regions within the composite, on the surface of the composite, or adjacent to the composite. The local pH is adjusted by the degradation products of bioceramic particles incorporated within or on the stent. The local pH is adjusted without administering alkalizing or acidic substances systemically to the patient. Systemic administration refers to administration that is accomplished orally or parenterally including intravascularly, rectally, intranasally, intrabronchially, or transdermally.

It is well known that the rate of corrosion reactions is dependent on the pH. In general, the rate of corrosion reactions is increased by decreasing the pH and decreased by an increase in pH. The rate of corrosion reactions increases as pH is lowered due to the higher concentration of hydrogen ions. The reverse tendency exists at higher pH because of the lower concentration of hydrogen ions. A higher pH means there are fewer free hydrogen ions to participate in corrosion reactions.

However, passivation, formation of a protective layer that reduces or stops corrosion, also depends on pH. This is due to the fact that solubility of the protective layer can depend on the pH. Thus, passivation depends on the solubility of the protective layer at the pH of the corrosive environment. Therefore, the pH dependence of the corrosion rate depends on both the rate of corrosion reactions and passivation. For example, the pH of the corrosive environment may increase or decrease with little or no change in corrosion rate due to passivation.

For example, it has been shown that in the range of pH 4 to pH 10, the corrosion rate of iron is relatively independent of the pH of the environment. For pH values below 4.0, FeO is soluble, thus, the oxide dissolves as it is formed rather than depositing on the metal surface to form a film. In the absence of the protective oxide film, the metal surface is in direct contact with the acid solution, and the corrosion reaction proceeds at a greater rate than it does at higher pH values. For pH values above about pH 10, the corrosion rate is observed to fall as pH is increased. This is believed to be due to the formation of a passive film of $Fe_2O_3$, which is less soluble than FeO. Therefore, decreasing the local pH of iron below 4 can accelerate its corrosion rate and increasing its local pH below 10 can decrease its corrosion rate.

Additionally, a gray oxide forms on the surface of unalloyed magnesium upon exposure to air at room temperature. Moisture converts this oxide to magnesium hydroxide, which is stable in the basic range of pH values, but is not in the neutral or acid ranges. In basic environments, passivation is possible as a result of the formation of a $Mg(OH)_2$ layer on the metal surface. The magnesium can still corrode in basic environments since the $Mg(OH)_2$ layer is slightly soluble. ASM Handbook, Volume 13A Corrosion: Fundamentals, Testing, and Protection (#06494G).

In some embodiments, bioceramic particles dispersed in the metal matrix can be biodegradable with basic or acidic degradation by-products. Upon implantation of a stent, the bioceramic particles can degrade and the degradation products can change the pH locally within or around the erodible metallic matrix.

In some embodiments, the degradation products change the local pH to a level that changes the corrosion rate of the metallic matrix. In such embodiments, the local pH is changed to a level that increases the corrosion rate. The increased corrosion rate may be due to decreased passivation, an increased rate of corrosion reactions, or both. As discussed above, the rate of corrosion reactions can be increased by decreasing the pH. In other such embodiments, the local pH level is changed to a level that decreases the corrosion rate. The decreased corrosion rate may be caused by increased passivation, decreased rate of corrosion reactions, or both. The decreased rate of corrosion reaction can be due to an increase in pH.

In certain embodiments, the erosion rate of the composite stent is modified through the use of dispersed bioceramic particles that have acidic degradation products. Such acidic degradation products can decrease the local pH in, around, or adjacent to the composite stent. In such embodiments, the erosion rate of a composite can be increased due to the decrease in pH. Thus, the erosion rate can be increased which decreases the degradation time of the stent. The degradation products decrease the pH to a level that increases the erosion rate of the composite. For example, tricalcium phosphate bioceramic particles and silica bioceramic particles release acidic degradation products that increase the degradation rate of a metal matrix.

In an exemplary embodiment, the metal matrix can be an iron or iron alloy with dispersed bioceramic particles having acidic degradation products that increase the erosion rate of the iron of a composite. In such embodiments, the local pH level is decreased sufficiently to increase corrosion rate. For example, the local pH level inside the stent can be decreased below 4 to increase the erosion rate.

In other embodiments, the erosion rate of a composite stent can be modified through the use of bioceramic particles that have basic degradation products. The basic degradation products can increase the local pH in, around, or adjacent to the composite stent. In such embodiments, the erosion rate of a composite can be decreased due to the increase in pH. Thus, the erosion rate can be decreased which increases the degradation time of the stent. The degradation products increase the pH to a level that decreases the erosion rate of the composite.

In certain embodiments, the local pH level within the stent can be adjusted by the concentration of bioceramic particles within the metal matrix. In such embodiments, the pH level can be adjusted lower by increasing the concentration of bioceramic particles with acidic degradation products. In other such embodiments, the pH level can be adjusted higher by increasing the concentration of bioceramic particles with basic degradation products.

In further embodiments, the composite can include a mixture of bioceramic particles that have acidic degradation products and basic degradation products. The relative amount of the types of particles can be adjusted to obtain a pH level that results in a desired corrosion rate. For example, increasing the relative concentration of bioceramic particles with acidic degradation products can decrease the pH level.

For example, a stent can formed from magnesium or a magnesium alloy with dispersed bioceramic particles that have basic degradation products. As an example, hydroxyapatite releases basic degradation products. In such embodiments, the dispersed bioceramic particles can decrease the erosion rate of a composite stent and increase its degradation time. It has been shown that a bioceramic metal matrix composite of AZ91D magnesium alloy with hydroxyapatite particles has a lower erosion rate than the AZ91D alloy alone. Biomaterials 28 (2007) 2163-2174.

In some embodiments, the concentration of bioceramic particles in the composite can be adjusted to obtain a selected erosion rate and degradation time of an erodible stent. Adjusting the concentration of bioceramic particles can change the erosion rate due to the both a change in pH level and the amount or mass of the metal matrix exposed to the degradation products. Exemplary embodiments of a composite of stent can have a concentration of bioceramic particles between 0.01 wt % and 30 wt %, 0.5 wt % and 30 wt %, 1 wt % and 30 wt %, 1 wt % and 20 wt %, or more narrowly, between 1 wt % and 5 wt %.

Additionally, the size of the bioceramic particles can be adjusted to tailor the erosion rate and degradation time. Bioceramic nanoparticles may be more effective in modifying the erosion rate of the metallic matrix than microparticles. Since nanoparticles have a larger surface to volume ratio than larger particles, they are expected to provide a greater and more uniform exposure to degradation products than larger particles.

In various embodiments of the invention, the dispersed bioceramic particles can act as a reinforcing material to enhance the mechanical properties of the matrix such as toughness, stiffness, and strength. In general, the higher the fracture toughness, the more resistant a material is to the propagation of cracks. Certain regions of an implantable medical device, such as a stent, experience a high degree of stress and strain when the device is under stress during use. For example, when a stent is crimped and deployed, curved or bending regions such as portions 130, 140, and 150 can have highly concentrated strain which can lead to fracture. The bioceramic particles can increase fracture toughness by reducing the concentration of strain by dispersing the strain over a larger volume of the material. Particles can absorb energy due to applied stress and disperse energy about a larger volume in the bioceramic metal matrix composite.

Therefore, rather than being highly concentrated, the stress and strain in a stent fabricated from a bioceramic metal matrix composite is divided into many small interactions involving numerous individual particles. When a crack is initiated in the material and starts traveling through the composite, the crack breaks up into finer and finer cracks due to interaction with the particles. Thus, the particles tend to dissipate the energy imparted to the stent by the applied stress.

Additionally, the use of nanoparticles may be particularly advantageous in improving mechanical properties. For a give weight ratio of particles to metal matrix, as the size of the particles decreases the number of particles dispersed throughout the stent per unit volume also increases. Thus, the number of particles available to disperse the energy of applied stress to the stent increases. Therefore, it is expected that a composite with nanoparticles will result in a more uniform and greater enhancement of mechanical properties.

Additionally, the dispersed bioceramic particles can increase the strength of the composite. As indicated above, a stent requires a high radial strength in order to provide effective support to a vessel. A composite having dispersed bioceramic particles with may have a higher strength than the metal matrix. It is believed that the bioceramic particles will enhance the strength and toughness during all or a portion of the time frame of erosion of a stent.

Furthermore, the use of bioceramic particles to tailor erosion and mechanical properties has advantages over prior methods of modifying such properties in erodible metal stents that adjust the metal composition. Specifically, the bioceramic particles provide an extra degree of freedom in controlling erosion and mechanical behavior. The metal matrix does not need to be selected or composition adjusted to have desired degradation properties since the properties can be adjusted through selection of the bioceramic particles.

In general, it is desirable for the bioceramic particles to be dispersed with high uniformity throughout the metallic matrix. A more uniform the dispersion of the particles results in more uniform properties of the composite and a device fabricated from the composite. For example, a uniform dispersion can result in a greater uniformity in the increase in toughness, modulus, strength, and degradation rate.

Types of Metals

In certain embodiments, the corrodible metal can be a metal that has a propensity for self-dissolution in an in vivo environment. A metal that undergoes self-dissolution in an in vivo environment corrodes when subjected to bodily fluids and breaks down. A self-dissolving metal can be selected that has little or no ill effect to a patient. Representative examples of self-dissolving metals in an in vivo environment include, but are not limited to, magnesium, manganese, calcium, zinc, chromium, iron, cadmium, aluminum, cobalt, antimony, tin, vanadium, copper, tungsten, and molybdenum.

In further embodiments, a stent can be fabricated from an alloy of one or more of the above-mentioned metals. Some alloys include a main constituent metal and a small amount one or more additional types of metals. The additional metals can also include biostable or nonerodible metals. In some exemplary embodiments, the elemental composition of the main constituent metal can be greater than 85%, 90%, 95%, or greater than 99% of the alloy. Main constituent metals are alloyed with additional metals to modify the corrosion rate, improve mechanical properties, or both.

Generally, the corrosion rate as a function of pH of an alloy is different from the component metals. In certain embodiments, the alloy composition and the type of bioceramic particles can be selected to provide a desired erosion rate. Thus, in such embodiments, an alloy composition can be adjusted to have a selected corrosion rate at a particular pH level corresponding to that provided by dispersed bioceramic particles.

In exemplary embodiments, magnesium can be alloyed with small of amounts of zinc, sodium, iron, potassium, calcium, aluminum, manganese, silver, zirconium, thorium, yttrium, and rhenium. In some exemplary embodiments, the magnesium composition can be greater than 85%, 90%, 95%, or greater than 99% of the alloy. For example, AZ91 magnesium alloy includes magnesium (89.8%), aluminum (9%), zinc (2%), and manganese (0.2%). In other commercial embodiments, magnesium can be alloyed with lithium with a magnesium-lithium ratio in the range of 60:40. Other magnesium alloys include AM50A and AE42. Additionally, zinc can be alloyed with titanium (0.1-1%) to improve fracture toughness since zinc is a comparative brittle material.

In further embodiments, the corridible metal may include a combination of two or more metals selected to create a galvanic couple such that the material will undergo galvanic dissolution upon contact with bodily fluids. Reliance on galvanic corrosion in order to achieve a desired corrosion rate requires the selection of a metal pair that has a sufficiently high rest potential differential. A rest potential differential results from two metals that, by themselves, each have a particular rest potential when measured versus a reference electrode, for example a Standard Calomel Electrode (SCE) or Natural Hydrogen Electrode (NHE), in the same type of solution, for example saline or equine horse serum. The driving force toward corrosion that results from this differential may be tailored to control the rate of degradation of the joined materials. For example, a driving force of about 500 mV would generally result in a slower dissolution than a driving force of 1 V or more.

In some embodiments, dispersed bioceramic particles can be used in combination with selected galvanic pairs to control the erosion rate of a composite stent. Appropriate metal pairs can be selected from among the elements magnesium, manganese, potassium, calcium, sodium, zinc, chromium, iron, cadmium, aluminum, cobalt, lead, vanadium, copper, and molybdenum, and from alloys based on such elements.

Bioceramics can include any ceramic material that is compatible with the human body. More generally, bioceramic materials can include any type of compatible inorganic material or inorganic/organic hybrid material. Bioceramic materials can include, but are not limited to, alumina, zirconia, apatites, calcium phosphates, silica based glasses, or glass ceramics, and pyrolytic carbons. Bioceramic materials can be bioabsorbable and/or active. A bioceramic is active if it actively takes part in physiological processes. A bioceramic material can also be "inert," meaning that the material does not absorb or degrade under physiological conditions of the human body and does not actively take part in physiological processes.

Illustrative examples of apatites and other calcium phosphates, include, but are not limited to hydroxyapatite ($Ca_{10}(PO_4)_6(OH)_2$), fluoroapatite ($Ca_{10}(PO_4)_6F_2$), carbonate apatide ($Ca_{10}(PO_4)_6CO_3$), tricalcium phosphate ($Ca_3(PO_4)_2$), octacalcium phosphate ($Ca_8H_2(PO_4)_6\text{-}5H_2O$) calcium pyrophosphate ($Ca_2P_2O_7\text{-}2H_2O$), tetracalcium phosphate ($Ca_4P_2O_9$), and dicalcium phosphate dehydrate ($CaHPO_4\text{-}2H_2O$).

The term bioceramics can also include bioactive glasses that are bioactive glass ceramics composed of compounds such as $SiO_2$, $Na_2O$, $CaO$, and $P_2O_5$. For example, a commercially available bioactive glass, Bioglass®, is derived from certain compositions of $SiO_2$—$Na_2O$—$K_2O$—$CaO$—$MgO$—$P_2O_5$ systems. Some commercially available bioactive glasses include, but are not limited to:

45S5: 46.1 mol % $SiO_2$, 26.9 mol % CaO, 24.4 mol % $Na_2O$ and 2.5 mol % $P_2O_5$;

58S: 60 mol % $SiO_2$, 36 mol % CaO, and 4 mol % $P_2O_5$; and

S70C30: 70 mol % $SiO_2$, 30 mol % CaO.

Another commercially available glass ceramic is A/W.

Bioceramic particles can be partially or completely made from a biodegradable, bioabsorbable, or biostable ceramic. Examples of bioabsorbable bioceramics include hydroxyapatite, various types of bioglass materials, tetracalcium phosphate, amorphous calcium phosphate, alpha-tricalcium phosphate, and beta-tricalcium phosphate. Biostable bioceramics include alumina and zirconia.

Further embodiments of the invention include formation of the bioceramic metal matrix composite and fabrication of an implantable medical device, such as a stent, therefrom. In some embodiments, the metal matrix composite can be formed by mixing the metal matrix with the bioceramic particles and extruding the mixture to form a construct, such as a tube. A stent can then be fabricated from the tube. For example, a stent pattern can then cut into the tube by laser cutting.

The mixing or extrusion process can be performed at low temperature, such as near room temperature (20-30° C.) or slightly elevated temperatures (<50° C. above room temperature). In other embodiments, the mixing or extrusion process can be performed at high temperature, for example, 50-75% of the melting temperature of the metal. In some embodiments, the mixing or extrusion are performed at temperatures above 75% of the melting temperature of the metal or greater than the melting temperature of the metal. The mixing or forming is performed at a temperature below the melting point of the bioceramic particles. The temperature can also be below a temperature at which the bioceramic particles significantly chemically degraded.

In some embodiments, the mixing and forming can be performed in the same apparatus. In such embodiments, the metallic particles or ingots and bioceramic particles can be fed into a mixing apparatus, such as an extruder, which both mixes and forms the construct. Alternatively, the composite mixture of metal and bioceramic particles can be mixed separately in one apparatus. For example, the composite can be formed in an extruder or batch mixer. In one embodiment, the bioceramic particles can be combined with a metal in a powdered or granular form prior to the mixing of the particles with the metal at an elevated temperature. The formed composite can then be fed into an extruder to form the tube.

Agglomeration or formation of clusters of bioceramic particles can reduce the uniformity of dispersion of the particles in the metal matrix. The agglomeration of bioceramic particles makes it difficult to disperse the particles within the composite. The presence of larger clusters in the composite tends to result in a decrease in material performance. Such larger clusters can result in the formation of voids in a composite portion of a stent, which are preferential sites for crack initiation and failure. The mechanical mixing in a conventional single screw extruder or in batch processing can be insufficient to break up the clusters, resulting in a nonuniform mixture of bioceramic particles and metal.

Various methods may be employed to increase the uniformity of dispersion of bioceramic particles within a metal matrix. Certain embodiments for decreasing agglomeration and increasing the dispersion of bioceramic particles in a composite can include processing a mixture of particles and metal with mechanical methods sufficient to reduce agglomeration. Such embodiments can include processing a mixture of a polymer and agglomerated bioceramic particles under high shear stress conditions. Some embodiments can include processing the mixture such that the particles are subjected to shear stress higher than the fracture strength of the agglomerated particles. In one embodiment, a metal can blended or mixed with bioceramic particles in a manner that subjects the mixture to a shear stress higher than the fracture strength of agglomerates of bioceramic particles. Thus, metal-bioceramic particle mixture can be processed so that a maximum shear stress generated during mixing is higher than the fracture strength of the bioceramic particle agglomerates. Agglomerated particles may be mechanically broken down and more uniformly dispersed within the metal.

It is believed that the shear stress produced by a single screw extruder is typically lower than the fracture strength of bioceramic particle agglomerates. Various kinds of mixing devices may be employed that can apply a shear stress higher than the fracture strength of agglomerates. Mechanical blending devices that can apply a sufficiently high shear stress include, but are not limited to, a twin screw extruder or kneader. During blending, once the shear stress is higher than the fracture strength of bioceramic particles agglomerates, the agglomerates are broken down and more uniformly dispersed into the metal. The metal and bioceramic particles can be fed into a mechanical blending device separately and processed at high shear stress. Alternatively, a composite mixture of metal and bioceramic particles can be fed into a mechanical blending device and processed at the high shear stress.

The bioceramic particle/metal mixture can be processed at the sufficiently high shear stress for a time sufficient to reduce agglomeration and disperse the particles. For example, the mixture can be processed between about 5 min. to about 30 min., more narrowly about 8 min. to about 20 min., or more narrowly about 10 min to about 15 min. In one embodiment, the composite formed with surface modified bioceramic particles can also be processed in this manner.

In general, good bonding between a matrix and a discrete or reinforcing phase in a composite material facilitates improvement of the mechanical performance of the composite. For example, the increase in the strength and toughness of composite due to the bioceramic particles can be enhanced by good bonding between the metal matrix and particles.

In some embodiments, bioceramic particles may include an adhesion promoter to improve the adhesion between the particles and the metal matrix. In one embodiment, an adhesion promoter can include a coupling agent. A coupling agent refers to a chemical substance capable of reacting with both the bioceramic particle and the metal matrix of the composite material. A coupling agent acts as an interface between the metal and the bioceramic particle to form a chemical bridge between the two to enhance adhesion.

The adhesion promoter may include, but is not limited to, silane and non-silane coupling agents. For example, the adhesion promoter may include 3-aminopropyltrimethoxysilane, 3-aminopropyltriethoxysilane, aminopropylmethyldiethoxy silane, organotrialkoxysilanes, titanates, zirconates, and organic acid-chromium chloride coordination complexes.

In some embodiments, the surface of the bioceramic particles may be treated with an adhesion promoter prior to mixing with the metal matrix. In one embodiment, the bioceramic particles can be treated with a solution containing the adhesion promoter. Treating can include, but is not limited to, coating, dipping, or spraying the particles with an adhesion promoter or a solution including the adhesion promoter. The particles can also be treated with a gas containing the adhesion promoter. In one embodiment, treatment of the bioceramic particles includes mixing the adhesion promoter with solution of distilled water and a solvent such as ethanol and then adding bioceramic particles. The bioceramic particles can then be separated from the solution, for example, by a centrifuge, and the particles can be dried. The bioceramic particles may then used to form a composite. In an alternative embodiment, the adhesion promoter can be added to the particles during formation of the composite. For example, the adhesion promoter can be mixed with a bioceramic/metal mixture during extrusion.

In some embodiments, the metal matrix of the bioceramic metal composite can be porous. The pores increase the surface area of contact of bodily fluids with both the metal matrix and the bioceramic particles. Therefore, there is increased corrosion of the metal and the bioceramic particles. Due to the increased surface area of contact, the pores tend to have an accelerating effect on the corrosion rate of the metal. It is expected that if the change in the pH due to bioceramic particles has an accelerating effect on the corrosion rate, the bioceramic particles will further accelerate the corrosion rate of the composite. However, if the change in the pH due to the bioceramic particles has a decelerating effect on the corrosion rate, the bioceramic particles may mitigate the accelerating effect of the pores. The rate of erosion can be tailored to a range of applications through selection of the metal, the degree of porosity, and the type of bioceramic particles.

The porosity has a substantial effect on the rate of corrosion to the extent that the ratio of corrosion rate increase to surface area increase has been found to vary from 0.3 to 1.0 depending on the type of material and the environment to which it is exposed. The morphology of the microcellular porous metal, including the cell size and porosity of the metal, can be controlled so that the cell sizes can be made very uniform, and can be controlled precisely by the manipulation of various parameters during the formation process. The desired porosity is achievable by a variety of techniques including, but not limited to sintering, foaming, extrusion, thixomolding, semisolid slurry casting and thermal spraying.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation.

"Strain" refers to the amount of elongation or compression that occurs in a material at a given stress or load.

"Elongation" may be defined as the increase in length in a material which occurs when subjected to stress. It is typically expressed as a percentage of the original length.

Elongation to Break is the strain on a sample when it breaks. It is usually is expressed as a percent.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLE

The example set forth below is for illustrative purposes only and are in no way meant to limit the invention. The following example is given to aid in understanding the invention, but it is to be understood that the invention is not limited to the particular materials or procedures of examples.

Magnesium Alloy/Nano Hydroxyapatite (HAP) Composite Stent Preparation

Step 1 Composite preparation: 1 kg of magnesium alloy is mixed with 100 g nano HAP at room temperature in a mechanical blender. The mixture is extruded through a signal or twin screw extruder with a puller at 400° C. The extruded tubing has an inside diameter 0.128 in and outside diameter=0.136 in.

Step 2 Stent preparation: The tubing is cut into a stent by a laser, and crimped to smaller diameter (0.05 in).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising a stent body consisting of a metal matrix composite, the composite including biodegradable bioceramic nanoparticles dispersed within and throughout a bioerodible metal matrix, wherein the bioceramic nanoparticles are spherical and have a diameter from 1 nm to 100 nm,
    wherein the biodegradable bioceramic nanoparticles that are dispersed modify the erosion rate of the stent body in a vascular environment and enhance mechanical properties of the stent body,
    wherein enhance the mechanical properties comprises an increase in tensile strength and an increase in fracture toughness,
    wherein erosion of the nanoparticles decreases the erosion rate of the metal,
    wherein the stent body is a scaffolding composed of a plurality of structural elements made from the composite, and
    wherein the bioceramic nano-particles are dispersed with high uniformity throughout the stent body and the bioceramic nanoparticles are dispersed throughout the scaffolding.

2. The stent of claim 1, wherein the nanoparticles have basic degradation products that increase a pH of a corrosive environment for the metal matrix, thereby decreasing the erosion rate of the metal matrix.

3. The stent of claim 1, wherein the composite comprises 1 wt % to 5 wt % of the bioceramic nanoparticles.

4. The stent of claim 1, wherein the nanoparticles comprise hydroxyapatite nanoparticles.

5. The stent of claim 1, wherein the metal is selected from the group consisting of magnesium and alloys thereof.

6. The stent scaffolding of claim 1, further comprising a coating on the surface of the stent body of the scaffolding including a polymer and a drug.

* * * * *